(12) United States Patent
Chon et al.

(10) Patent No.: US 8,388,543 B2
(45) Date of Patent: Mar. 5, 2013

(54) PHOTOPLETHYSMOGRAPHY APPARATUS AND METHOD EMPLOYING HIGH RESOLUTION ESTIMATION OF TIME-FREQUENCY SPECTRA

(75) Inventors: Ki H. Chon, Mount Sinai, NY (US); Kilwan Ju, Whitestone, NY (US)

(73) Assignee: The Research Foundation of State University of New York, Albany, NY (US)

( * ) Notice: Subject to any disclaimer, the term of this patent is extended or adjusted under 35 U.S.C. 154(b) by 1662 days.

(21) Appl. No.: 11/803,770

(22) Filed: May 16, 2007

(65) Prior Publication Data

US 2008/0287815 A1    Nov. 20, 2008

(51) Int. Cl.
*A61B 5/02* (2006.01)
(52) U.S. Cl. ........ 600/500; 600/484; 600/504; 600/509; 600/529
(58) Field of Classification Search .......... 600/300–301, 600/323, 500–507; 702/75–76; 375/240.18–240.19
See application file for complete search history.

(56) References Cited

U.S. PATENT DOCUMENTS

| | | | | |
|---|---|---|---|---|
| 6,862,558 | B2 * | 3/2005 | Huang | 702/194 |
| 2005/0070774 | A1 * | 3/2005 | Addison et al. | 600/323 |
| 2006/0200035 | A1 * | 9/2006 | Ricci et al. | 600/513 |
| 2006/0211930 | A1 * | 9/2006 | Scharf et al. | 600/336 |

OTHER PUBLICATIONS

Wang et al. "A High Resolution Approach to Estimating Time-Frequency Spectra and Their Amplitudes" Annals of Biomedical Engineering, vol. 34, No. 2, Feb. 2006 pp. 326-338.*
Gasquet and Wooton."Variable-frequency complex demodulation technique for extracting amplitude and phase information." Rev. Sci. Instrum. 68 (1), Jan. 1997, 1111-1114.*
Peng et al. "An improved Hilbert—Huang transform and its application in vibration signal analysis" Journal of Sound and Vibration 286 (2005) 187-205.*
Monitoring of the heart and respiratory rates by photoplethysmography using a digital filtering technique; K. Nakajima, T. Tamura and H. Miike; Medical Eng. Phys. vol. 18, No. 5 pp. 365-372 Jul. 21, 1995 (8pp).
A Robust Time-Varying Identification Algorithm Using Basis Functions; Rui Zou, Hengliang Wang, and Ki H. Chon; Annals of Biomedicial Engineering, vol. 31, pp. 840-853 Mar. 12, 2003 (14pp).

* cited by examiner

*Primary Examiner* — Michael Kahelin
*Assistant Examiner* — Eric Messersmith
(74) *Attorney, Agent, or Firm* — The Farrell Law Firm, P.C.

(57) ABSTRACT

A photoplethysmography apparatus and method is provided for high resolution estimating of Time-Frequency Spectra (TFS) and associated amplitudes using Variable Frequency Complex Demodulation (VFCDM), in a two-step procedure using a Time-Varying Optimal Parameter Search (TVOPS) technique to obtain TFS, followed by VFCDM to obtain even greater TFS resolution and instantaneous amplitudes associated with only specific frequencies of interest, via the combined TVOPS and VFCDM.

7 Claims, 16 Drawing Sheets

PHOTOPLETHYSMOGRAPHY APPARATUS AND METHOD EMPLOYING HIGH RESOLUTION ESTIMATION OF TIME-FREQUENCY SPECTRA

GOVERNMENT SUPPORT

The invention was made with government support under grant number NL069629 awarded by the National institutes of Health. The U.S. Government has certain rights in the invention.

PRIORITY

This application claims priority to application Ser. No. 60/800,772 filed with the U.S. Patent and Trademark Office on May 16, 2006.

BACKGROUND OF THE INVENTION

1. Field of the Invention

The present invention relates generally to photoplethysmography ("PPG") and, more particularly, to a method and apparatus for extraction of respiratory rate from pulse oximetry data for patient care.

2. Background of the Related Art

For patients at risk of cardio-respiratory failure, it is important to monitor the efficiency of gas exchange in the lungs, that is, the oxygenation of arterial blood flow. Pulse oximetry provides a non-invasive means to monitor arterial oxygen saturation ($SaO_2$) on a continuous basis, based on photoplethysmography techniques used in patient monitors during anesthesia and in intensive care units. For example, see U.S. Pat. No. 7,169,110 to Lee, et al., the contents of which are incorporated herein by reference.

Pulse oximeters can be used to measure both $SaO_2$ and basic cardiac function (e.g., heart rhythms). In addition to being simple to operate, pulse oximeters are non-invasive and do not create any discernable patient discomfort. Respiratory rate is important for many clinical uses, including prevention of sleep apnea, sudden infant death syndrome (SIDS) and chronic obstructive pulmonary disease. Patient respiratory rate, even the respiratory rate of an infant, can be extracted from pulse oximetry, as the pulse oximeter signal includes both heart rate and respiratory signal data.

Present practice for automatic respiration rate measurement requires monitoring of $CO_2$ production using a capnograph. However, the capnograph is an expensive device that requires a significant amount of maintenance. In addition, the capnograph requires a mask or nasal cannula, and is therefore obtrusive to the patient and cumbersome to use. Accordingly, there is a need for a less intrusive method for obtaining accurate respiratory rates, such as by use of pulse oximeters, in addition to $SaO_2$ data.

In the present invention, respiratory rate is obtained by detecting the presence of baseline, amplitude and frequency modulations. However, prior efforts in this field have found it difficult to detection the modulations, due to myriad causes. Three primary culprits stand out: the time-varying nature of these modulations; the often subtle nature of both amplitude and frequency modulations, thus creating a need for a highest possible time and frequency resolution for detection; and masking by motion and noise artifacts of amplitude and frequency modulations. Also see discussion of shortcomings outlined by Nakajima, et al., *Monitoring of Heart and Respiratory Rates by Photoplethysmography Using a Digital Filtering Technique*, Med. Eng. Phy. Vol. 18, No. 5, pp. 365-372 (1996). The present invention overcomes the difficulty encountered by conventional systems, including the system suggested by Nakajima, et al., in obtaining data regarding respiratory rate and arterial blood flow oxygenation.

Past and on-going research efforts have analyzed Time-Varying (TV) signals and Short Time Fourier Transform (STFT) algorithms in an effort to obtain a simple to implement solution. However TV signals and STFT algorithms cannot provide simultaneous high time-frequency resolution.

A Wigner-Ville distribution approach, which is one of the Cohen class time-frequency spectral methods, can provide one of the highest time and frequency resolutions. However, the Wigner-Ville distribution approach is limited in the creation of artificial cross terms in the case of signals with multi-frequency components. Efforts to curtail undesired cross terms with the Wigner-Ville distribution have resulted in many different techniques, all based on utilizing either or both time and frequency windows. The consequence of using either time or frequency domain is a degradation of resolution in the other domain (frequency or time, respectively). That is, the aforementioned methods fix both time and frequency resolutions.

A recently introduced Time-Frequency (TF) spectral method, Hilbert-Huang Transform (HHT), provides both high time and frequency resolutions. The HHT is based on combinational use of empirical mode decomposition and Hilbert transform. Because the HHT does not rely on the use of the Fourier transform, concomitant high TF resolution can be obtained. However, capability of the HHT degrades in tandem with increasing levels of noise contamination.

The above-described conventional methods are known as nonparametric approaches, since they do not characterize data into a model where a few sets of parameters are used to capture essential features of the data. Most nonparametric approaches require sufficiently long data record lengths.

Parametric methods, in contrast, are useful for analyzing short data records and provide concomitant high TF resolution without any unwanted cross terms in multicomponent signals. Some autoregressive model-based TF spectral methods include the recursive least squares, least mean squares, and Kalman filter. These methods can adaptively track slowly TV dynamics, which are represented by a few parameters from which Time-Frequency Spectra (TFS) can be obtained. However, these methods are limited in that they are more suitable for slow TV signals and are sensitive to the choice of the number of model coefficients.

Accordingly, a Time-Varying Optimal Parameter Search (TVOPS) has been developed to alleviate sensitivity to model order choice and to provide high time-frequency resolution even for short data records. A limitation exists, however, as it does not preserve amplitudes of TFS, as is the case with all parametric TFS methods.

While Complex DeModulation (CDM), which does preserve instantaneous amplitudes, has been previously used for amplitude-modulating signals and applied to instantaneous frequency estimation, its application to TFS has not yet been fully explored. CDM assumes that only a single frequency is present within a predefined frequency band that may not be arbitrarily small, which is a limitation. Consequently, the TF resolution is not optimal. To overcome this limitation, a version of CDM has been developed in the present invention that uses variable frequencies, providing high time-frequency resolution as well as preservation of the amplitudes of TFS. This aim is motivated by the fact that no single algorithm is able to provide concomitant high time-frequency resolution as well as preservation of the amplitude distribution of the signal. This approach has two steps, in which the TVOPS is utilized to obtain TFS and then the Variable Frequency Complex DeModulation (VFCDM) is used to obtain even more accurate TFS and amplitudes of the TFS. The inventive combination of the TVOPS and VFCDM provides higher TF resolution than most other TFS approaches, in addition to preserving amplitude distributions of the TF spectra.

Recent efforts that use advanced signal processing algorithms in an attempt to overcome the aforementioned problems have used a series of adaptive Low Pass Filters (LPF) followed by High Pass Filters (HPF) with suitable cut-off frequencies, as described by Nakajima et al. These efforts, however, are able to distinguish heart and respiratory signals in the PPG signal, and accuracy degrades with motion artifacts, which are especially prevalent in the PPG signal during exercise. Furthermore, the cutoff frequencies of the LPF and HPF must be individually tailored, precluding wide clinical use.

New techniques that estimate time-frequency spectra for analyzing non-stationary signals utilize STFT and a Continuous Wavelet Transform (CWT) to extract respiratory rate from the PPG signals. However, success of these techniques is predicated on obtaining the highest possible time and frequency resolution, which is not possible with either the STFT or the CWT. It is widely known that the CWT cannot provide concomitant high time and frequency resolution as it only provides high frequency resolution at low frequencies and high time resolution at high frequencies.

For subjects with chronic obstructive pulmonary disease, reflection of respiratory rate via the amplitude and frequency modulations of a PPG signal is often subtle, as physical limitations often preclude these subjects from breathing in a normal manner. It is unclear what is considered "low frequency" because the low frequency range can vary depending on the dynamics of the system. Furthermore, real-time implementation is especially challenging for the CWT. Despite recent advances to improving accuracy of PPG signals and advanced signal processing algorithms, a method does not exist that allows an apparatus to accurately determine respiratory rate from pulse oximeter data.

Accordingly, the present invention overcomes limitations of conventional systems by applying a new algorithm that accurately extracts continuous respiratory rate from noninvasive recordings of PPG signals. The algorithm utilizes a highest possible time and frequency resolution approach to estimate TFS and associated amplitudes via use of VFCDM, which provides the highest time and frequency resolution and most accurate amplitude estimates as compared to smoothed pseudo Wigner-Ville, continuous wavelet transform and Hilbert-Huang transform methods. Thus, the VFCDM algorithm is significantly more accurate than the power spectral density, CWT and other conventional time-frequency based methods for determining respiratory rate.

SUMMARY OF THE INVENTION

A high-resolution approach to estimating TFS and associated amplitudes via the use of VFCDM is presented. This two-step procedure utilizes the TVOPS technique to obtain TFS, followed by using the VFCDM to obtain greater TFS resolution and instantaneous amplitudes associated with only the specific frequencies of interest. This combinational use of the TVOPS and the VFCDM is referred to herein as TVOPS-VFCDM, which provides highest resolution and most accurate amplitude estimates when compared to the smoothed pseudo Wigner-Ville, continuous wavelet transform and Hilbert-Huang transform methods.

In addition, the TVOPS-VFCDM to renal blood flow data provides a quantitative approach to understanding the dynamics of renal auto regulatory mechanisms and for quantitatively discriminating between different strains of rats.

The present invention is utilized to provide an apparatus for determining renal blood flow data, by providing a controller for estimating TFS and associated amplitudes using VFCDM, wherein the TVOPS is first utilized to obtain the TFS and the VFCDM is then utilized to obtain greater TFS resolution and instantaneous amplitudes associated with only specific frequencies of interest.

The present invention allows for improved diagnosis and treatment of sleep apnea, replacement electrocardiograph signal, sudden infant death syndrome, and hypovolemia and hypovolumic conditions.

BRIEF DESCRIPTION OF THE FIGURES

The above and other objects, features and advantages of certain exemplary embodiments of the present invention will be more apparent from the following detailed description taken in conjunction with the accompanying drawings, in which.

DETAILED DESCRIPTION OF THE PREFERRED EMBODIMENTS

Figure 1:
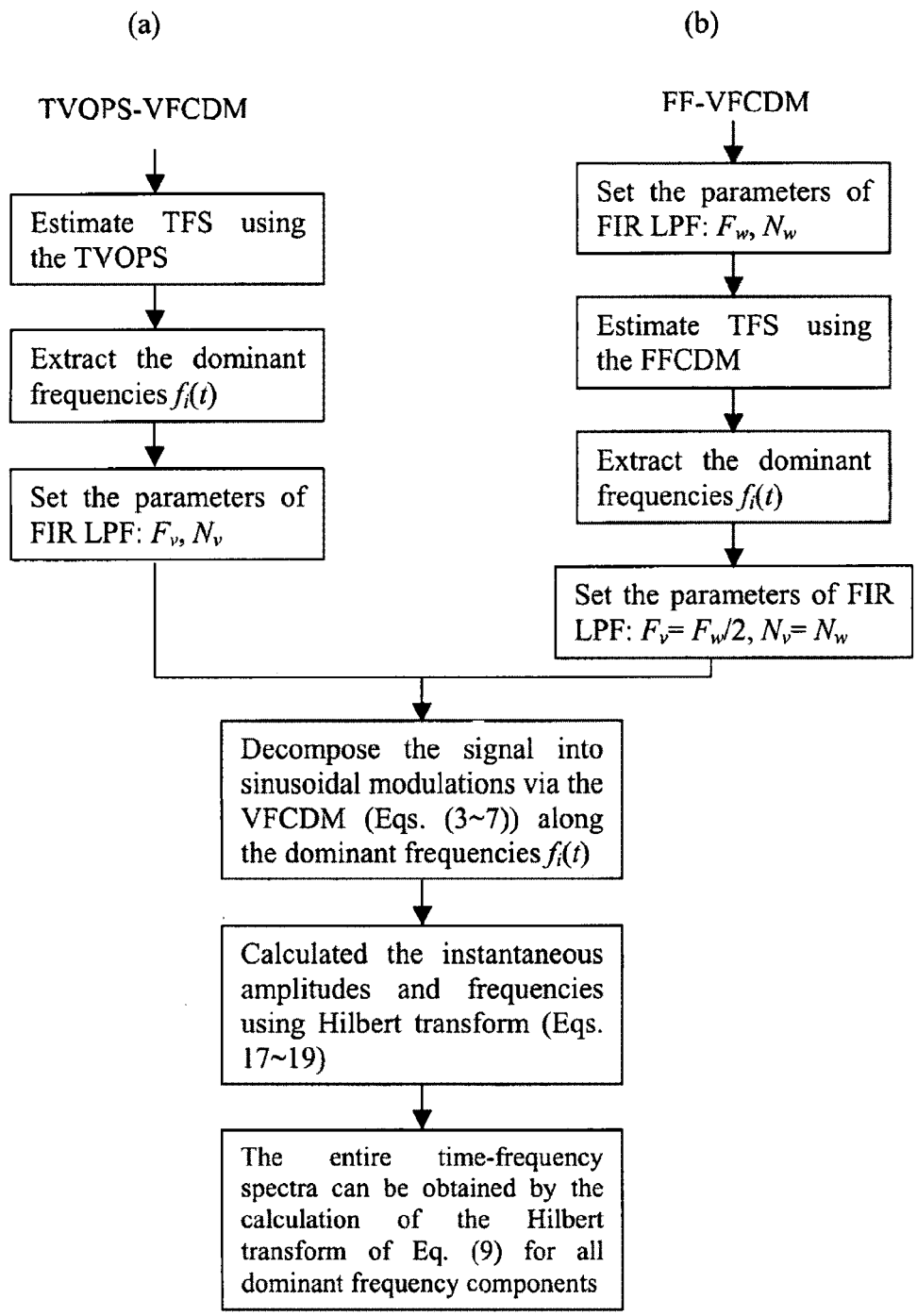
FIG. 1 is a flowchart of a procedure for calculating TVOPS-VFCDM and FF-VFCDM.

A description of detailed construction of preferred embodiments is provided to assist in a comprehensive understanding of exemplary embodiments of the invention. Accordingly, those of ordinary skill in the art will recognize that various changes and modifications of the embodiments described herein can be made without departing from the scope and spirit of the invention. Descriptions of well-known functions and constructions are omitted for clarity and conciseness.

In regard to complex demodulation methods for estimating TFS, a sinusoidal signal x(t) is considered to be a narrow band oscillation with a center frequency $f_o$, instantaneous amplitude A(t), phase $\phi(t)$, and the direct current component dc(t), as in Equation (1):

$$x(t)=dc(t)+A(t)\cos(2\pi f_o t+\phi(t)) \quad (1)$$

For a given center frequency, instantaneous amplitude information A(t) and phase information φ(t) can be extracted by multiplying Equation (1) by $e^{-j2\pi f_0 t}$, resulting in Equation (2):

$$z(t) = x(t)e^{-j2\pi f_0 t} = dc(t)e^{-j2\pi f_0 t} + \frac{A(t)}{2}e^{j\phi(t)} + \frac{A(t)}{2}e^{-j(4\pi f_0 t + \phi(t))} \quad (2)$$

A leftward shift by $e^{-j2\pi f_0 t}$ results in moving the center frequency, $f_0$, to zero frequency in the spectrum of z(t). If z(t) in Equation (2) is subjected to an ideal Low-Pass Filter (LPF) with a cutoff frequency $f_c < f_0$, then the filtered signal $z_{lp}(t)$ will contain only the component of interest and the following Equations (3-5) are obtained:

$$z_{lp}(t) = \frac{A(t)}{2}e^{j\phi(t)} \quad (3)$$

$$A(t) = 2|z_{lp}(t)| \quad (4)$$

$$\phi(t) = \arctan\left(\frac{\text{imag}(z_{lp}(t))}{\text{real}(z_{lp}(t))}\right) \quad (5)$$

When a modulating frequency is not fixed, as described above, but varies as a function of time, the signal x(t) can be written in the following form of Equation (6):

$$x(t) = dc(t) + A(t)\cos\left(\int_0^t 2\pi f(\tau)d\tau + \phi(t)\right) \quad (6)$$

Similar to the operations in Equations (1-2), multiplying Equation (6) by $$e^{-j\int_0^t 2\pi f(\tau)d\tau}$$

yields both instantaneous amplitude, A(t), and instantaneous phase, φ(t), as described in Equation (7):

$$z(t) = x(t)e^{-j\int_0^t 2\pi f(\tau)d\tau} = \quad (7)$$
$$dc(t)e^{-j\int_0^t 2\pi f(\tau)d\tau} + \frac{A(t)}{2}e^{j\phi(t)} + \frac{A(t)}{2}e^{-j(\int_0^t 4\pi f(\tau)d\tau + \phi(t))}$$

From Equation (7), if z(t) is filtered with an ideal LPF with a cutoff frequency $f_c < f_0$, then the filtered signal $z_{lp}(t)$ will be obtained with the same instantaneous amplitude A(t) and phase φ(t) as provided in Equations (4-5). The instantaneous frequency is given by Equation (8):

$$f(t) = f_0 + \frac{1}{2\pi}\frac{d\phi(t)}{dt} \quad (8)$$

For a variable frequency, the center frequency, $f_0$, is replaced with a variable frequency. In the preset invention a center frequency is first used to estimate instantaneous frequency within the arbitrarily set frequency band using Equation (8). It is reasonable to expect instantaneous frequencies that are changing, especially if the dynamics are highly TV. Thus, a subsequent variable frequency approach is utilized, which accounts for the possible TV nature of instantaneous frequency within the defined frequency bands to obtain a more precise measurement of instantaneous frequency. As described in further detail below, using a combination of fixed and variable frequencies instead of only the fixed frequency approach is advantageous over conventional techniques.

In regard to Equations (1)-(6) above, changing the center frequency followed by using the variable frequency approach of Equation (1) and Equation (6), respectively, as well as the LPF, the signal, x(t), will be decomposed into the sinusoid modulations by the CDM technique, as in Equation (9):

$$x(t) = \sum_i d_i = dc(t) + \sum_i A_i(t)\cos\left(\int_0^t 2\pi f_i(\tau)d\tau + \phi_i(t)\right) \quad (9)$$

The instantaneous frequency and amplitude of di is then calculated using a Hilbert transform. The entire time-frequency spectrum can be obtained by the calculation of the Hilbert transform of Equation (9) for all time points for the obtained low-pass filtered frequency components, as described in Equation (3). Therefore, by the combination of the CDM and Hilbert transform, a high TF resolution spectrum and accurate amplitude information is obtained.

The procedure for implementing the CDM on a TFS is summarized immediately below and discussed in further detail herein.

1) Design a Finite Impulse Response (FIR) LPF with the bandwidth and the length of the filter set to $F_\omega$, and $N_\omega$, respectively. Set center frequencies, $f_{0_i} = (i-1)(2F_\omega)$;

$$i = 1, \ldots, \text{int}\left(\frac{\max freq}{2F_\omega}\right),$$

where the bandwidth between neighboring center frequencies is $2 \times F_\omega$, and max freq represents the highest signal frequency.

2) Use the fixed frequency of the CDM to extract the dominant frequency within the confined bandwidth and repeat it over the entire frequency band (by incrementing $f_{0_i}$), referred to herein as Fixed-Frequency Complex Demodulation (FFCDM).

3) Decompose the signal into sinusoidal modulations via the CDM.

4) Calculate instantaneous frequencies (see Equation (19) below) based on the phase (Equation (18) below) and instantaneous amplitudes (Eq. (17) below) of each sinusoidal modulation component using the Hilbert transform.

5) Obtain TF representation of the signal using the estimated instantaneous frequencies and amplitudes.

6) For a variable frequency method, the first step is to use any of the time-frequency approaches (e.g., TVOPS, FFCDM, or smoothed pseudo Wigner-Ville (SPWV)) to obtain an estimate of the TFS. The center frequencies are the "backbones" of the time-frequency spectra, and only they are considered in subsequent analysis. This approach allows a considerable reduction in computation time since only a few frequencies (those of interest) are analyzed.

The FIR LPF has a filter bandwidth set to $F_v=F_\omega/2$, and a length of the filter is set to $N_v=N_w$ along estimated center frequencies $f_i(t)$. Further refined amplitude and phase information is extracted via steps 3-5, above, thereby further improving performance of any of the TFS including the FFCDM and TVOPS, and further improved time-frequency resolution is obtained.

Step 6 above is referred to herein as VFCDM, which is a two-step procedure, in which the first procedure involves using any of the time-frequency methods (e.g., TVOPS or FFCDM). The TVOPS is a recently developed algorithm THAT provides one of the most accurate TF spectra, mainly due to an accurate model order selection criterion. Zou, R., et al., *A Robust Time-Varying Identification Algorithm Using Basis Functions*, Ann. Biomed. Eng., 31:840-53 (2003), generally describes the TVOPS. Choosing the FFCDM followed by the VFCDM is referred to as FF-VFCDM. Similarly, use of the TVOPS followed by the VFCDM is termed TVOPS-VFCDM. A flowchart of a procedure for calculating TVOPS-VFCDM and FF-VFCDM is provided at FIG. 1. Advantages of the VFCDM over the FFCDM are shown in FIG. 2A-C.

A chirp signal is considered (the length is 1024 points, and frequencies are linearly increasing from 0 Hz to 0.5 Hz with the sampling rate set at 1 Hz). The FFCDM and VFCDM techniques are used to estimate the frequency and amplitude of the chirp signal. For illustration purposes, consider only the center frequency at $f_0=0.25$ Hz (instead of the entire set of center frequencies) and the LPF cutoff frequency are set at $f_c=0.02$ Hz.

Figure 2:
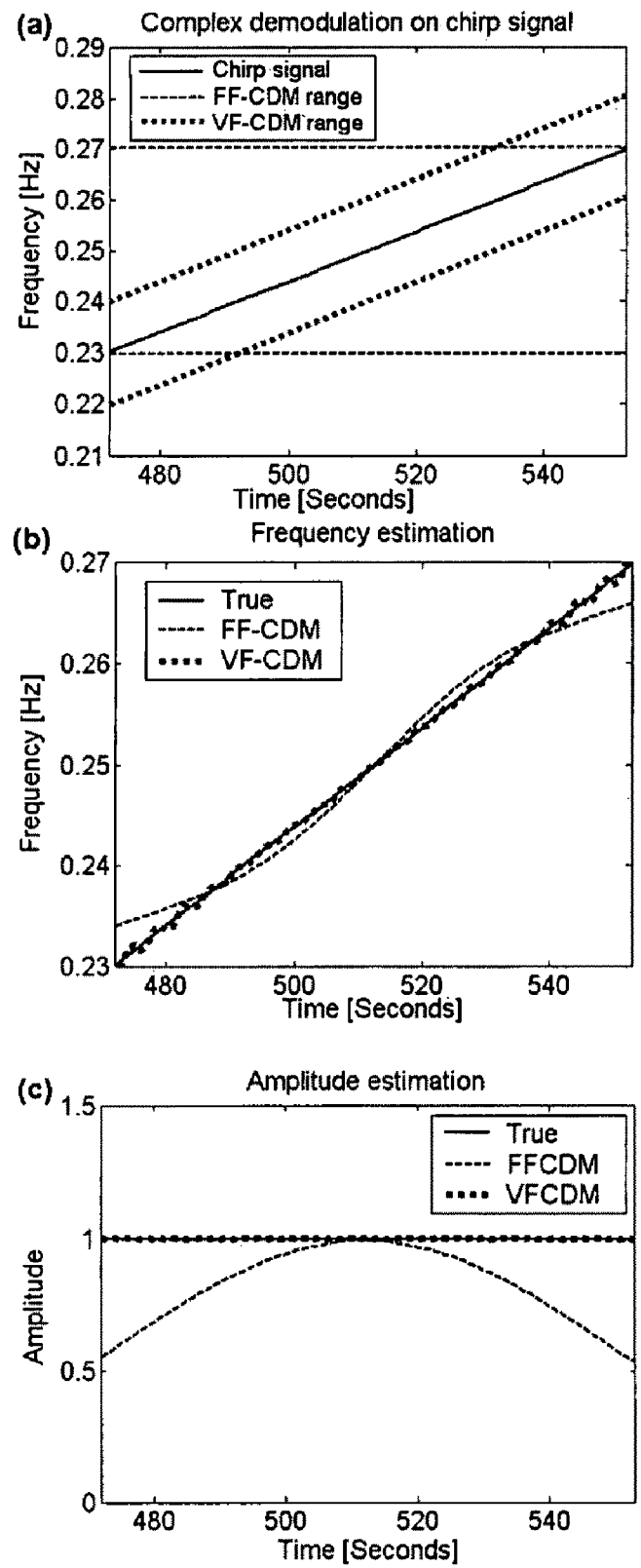
FIGS. 2A-C show an advantage of the VFCDM over a Fixed Frequency Complex DeModulation (FFCDM)

Due to the setting of the center and LPF cutoff frequencies, the FFCDM attempts to find the frequencies and amplitudes within the bandwidth demarcated by the paired horizontal dashed lines in FIG. 2. With the VFCDM, because an estimate of the center frequencies via any of the time-frequency methods (e.g., TVOPS or FFCDM) is provided, the filter bandwidths can be further reduced (e.g., $f_c=0.01$ Hz instead of $f_c=0.02$ Hz for the FFCDM) and are parallel to the chirp signal. The dashed (FFCDM) and dotted (VFCDM) lines in FIGS. 2B-C represent an estimation of an exact (solid line) instantaneous frequency and amplitude of the chirp signal, respectively.

As shown in FIGS. 2B-C, the results from the VFCDM are more accurate than those of the FFCDM. Note that in general, because the VFCDM is a two-step procedure, it will provide more accurate results than will the FFCDM. The example provided highlights an important issue: when frequencies of interest oscillate with time (i.e., are not a constant value for all time) then the FFCDM will suffer from edge effects of the LPF.

An edge effect arises when the frequency is close to $f_0 \pm f_c$ (at the beginning and end time points shown in FIG. 2A with the FFCDM), since a LPF is not the ideal filter with a perfect linear group delay and flat pass band. However, with the VFCDM, the edge effect is less of a concern as the LPF filter bandwidth hugs along the center frequencies. Therefore, this also contributes to the greater accuracy of the VFCDM than the FFCDM.

Properties of Time-frequency Presentations of Complex Demodulation are now addressed. By taking the Hilbert transform of x(t) in Equation (1), above, we obtain the following Equation (10):

$$s(t)=x(t)+j\text{Hilbert}[x(t)] \quad (10)$$

where s(t) is the analytic signal (real and imaginary) of x(t). $S_t(\omega)$ is denoted as the TFS of the signal obtained by the CDM. The properties of the TFS representation of the CDM are defined below.

Turning now to the completeness of CDM. As CDM decomposes the signal, the completeness of CDM is provided by the summation of all decomposed signals, as in Equation (11):

$$x(t) = \sum_i d_i(t) \quad (11)$$

The total energy of the distribution is obtained by integrating over all time and frequencies, as in Equation (12):

$$\int |s(t)|^2 dt = \int s(t)s^*(t)dt = \iiint S_t(\omega) S_t^* (\omega') e^{j(\omega-\omega')t} d\omega d\omega' dt = \iint |S_t(\omega)|^2 d\omega dt \quad (12)$$

Marginals can be defined for time and frequency conditions. The time marginal refers to the instantaneous energy, obtained by summing up the energy distribution for all frequencies at a particular time. The frequency marginal refers to the energy density spectrum, obtained by summing up the energy distribution over all times at a particular frequency. CDM spectral analysis satisfies the time marginal, as summing up for all frequencies at a particular time provides the instantaneous energy, as in Equation (13):

$$P(t)=\int |S_t(\omega)|^2 d\omega = \iint S_t(\omega) S_t^*(\omega') e^{j(\omega-\omega')t} d\omega d\omega' = |s(t)|^2 \quad (13)$$

The CDM does not satisfy the frequency marginal, as in Equation (14).

$$P(\omega)=\int |S_t(\omega)|^2 dt \neq |S(\omega)|^2 \quad (14)$$

However, for a particular bandwidth (BW, i.e. the frequency range of each decomposed signal), the frequency marginal is satisfied, as in Equation (15):

$$P(BW) = \int\int_{BW} |S_t(\omega)|^2 d\omega dt = \int_{BW} |S(\omega)|^2 \quad (15)$$

Turning now to time-frequency resolution. The FFCDM and VFCDM are based on calculation of instantaneous frequencies via the Hilbert transform, thus the time and frequency tradeoffs associated with the Fourier transform do not apply. Thus, simultaneous high time and frequency resolution can be obtained. If the bandwidth of the filter is arbitrarily designed to be small, then there is an increasing probability that only a single frequency will be present. In this case the instantaneous frequency will most likely represent the true frequency. If not, the instantaneous frequency will be the composite of the multi-frequency components. Therefore, the smaller the filter bandwidth, the greater the likelihood that the instantaneous frequency represents the true frequency.

Turning now to a combination of the TVOPS and VFCDM (TVOPS-VFCDM). The TVOPS algorithm is based on estimating only a few time-varying coefficients that best characterize the dynamics of the system to within a specified degree of accuracy, and is briefly described as follows.

In the Hilbert Transform, for an arbitrary time series, X(t), it is assumed that X(t) contains center frequency oscillations, i.e., $f_0$. The Hilbert transform, Y(t), is as provided in the following Equation (16):

$$Y(t) = H[X(t)] = \frac{1}{\pi} \int \frac{X(t')}{t-t'} dt' \quad (16)$$

An instantaneous amplitude is provided in Equation (17):

$$A(t)=[X^2(t)+Y^2(t)]^{1/2} \quad (17)$$

and an instantaneous phase is provided in Equation (18):

$$\varphi(t) = \arctan\left(\frac{Y(t)}{X(t)}\right) \quad (18)$$

The instantaneous frequency is provided in Equation (19):

$$f(t) = \frac{1}{2\pi}\frac{d\varphi(t)}{dt} \quad (19)$$

The above-referenced TVOPS method is based on estimating only a few time-varying coefficients that best characterize the dynamics of the system to within a specified degree of accuracy. Thus, the resulting time-varying spectra are not data length dependent, meaning that they are high-resolution time-frequency spectra, which are immune from cross-term spectral artifacts when there are multiple components in the signal. To obtain TV spectra, the data are formulated into a time-varying autoregressive (TVAR) model of the form of Equation (20-a):

$$y(n) = \sum_{i=1}^{P} a(i,n)y(n-i) + e(n) \quad (20\text{-}a)$$

where a(i,n) are the TVAR coefficients to be determined, and are functions of time. Index P is the maximum order of the AR model. The term e(n) is the residual error. The TVAR coefficients are expanded onto a set of basis functions and then the optimal parameter search algorithm is used to select only the significant TV terms among the chosen P terms. The next step is then to use either the least squares or total least squares methods to estimate TV coefficients.

After obtaining the TV coefficients a(i,n), the TV spectrum, S(n,ω) is calculated utilizing Equation (20-b):

$$S(n,\omega) = \frac{T}{\left|1 + \sum_{k_1=1}^{P} a(k_1,n)e^{-jwTk_1}\right|^2} \quad (20\text{-}b)$$

While the TVOPS provides one of the highest possible time and frequency resolutions possible compared to other methods, it does not preserve amplitude information since it is based on a time-varying autoregressive model. Thus, the TVOPS is first used to find frequency content and then the VFCDM technique to estimate the amplitude information related to the frequency content. This combination, termed, TVOPS-VFCDM, provides one of the highest TF resolutions as well as accurate estimation of the amplitudes, as discussed in detail herein.

In regard to the present invention, simulation results were obtained involving the combined use of the TVOPS-VFCDM, and these simulation results are discussed below and shown in the appended figures. To illustrate the technical advantages of the approach, comparison to Smoothed Pseudo Wigner-Ville (SPWV), Continuous Wavelet Transform (CWT), HHT, FFCDM, FF-VFCDM and the sole use of the TVOPS are made. Time-frequency spectra to be shown are in a logarithmic scale. The data length was 1024 points with a sampling rate of 1 Hz. For the SPWV, the Hamming windows were chosen for both time averaging and frequency smoothing to attenuate cross terms. The length of time and frequency smoothing window was 1/10 and 1/4 of the data length, respectively. For the CWT, the Morlet wavelet was chosen with the lowest and highest frequencies set to 0.01 Hz and 0.5 Hz, respectively.

Figure 3A:
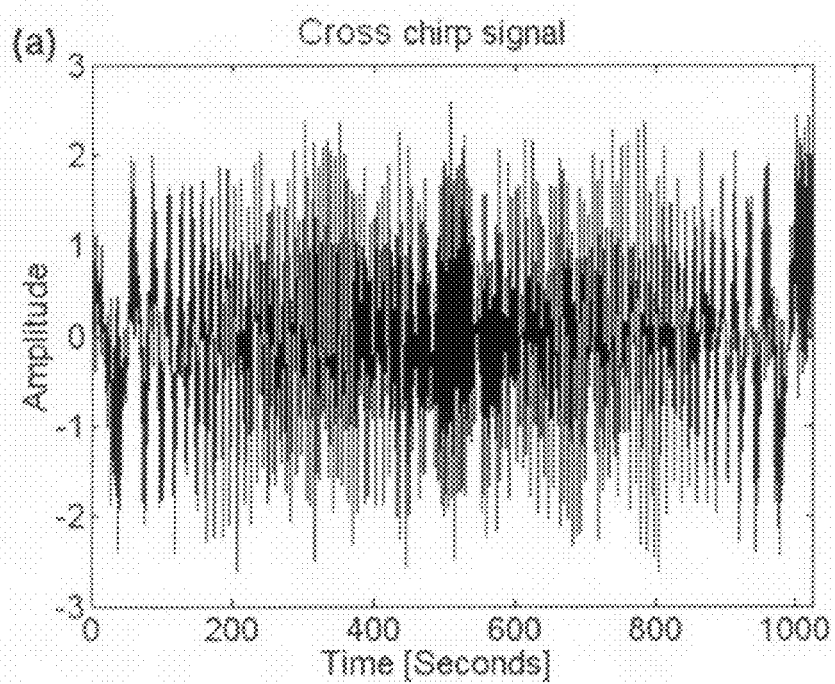
FIGS. 3A-H provide a time-frequency analysis of a cross chirp signal contaminated by 10 dB additive Gaussian white noise.

For a first example, a cross chirp signal (frequencies that are both linearly increasing and decreasing) with 10 dB additive Gaussian white noise is considered, and is shown in FIG. 3a. Estimated time-frequency spectra of the SPWV, CWT, HHT, FFCDM, FF-VFCDM, TVOPS, and TVOPS-VFCDM are shown in FIGS. 3B-H, respectively.

Figure 3B:
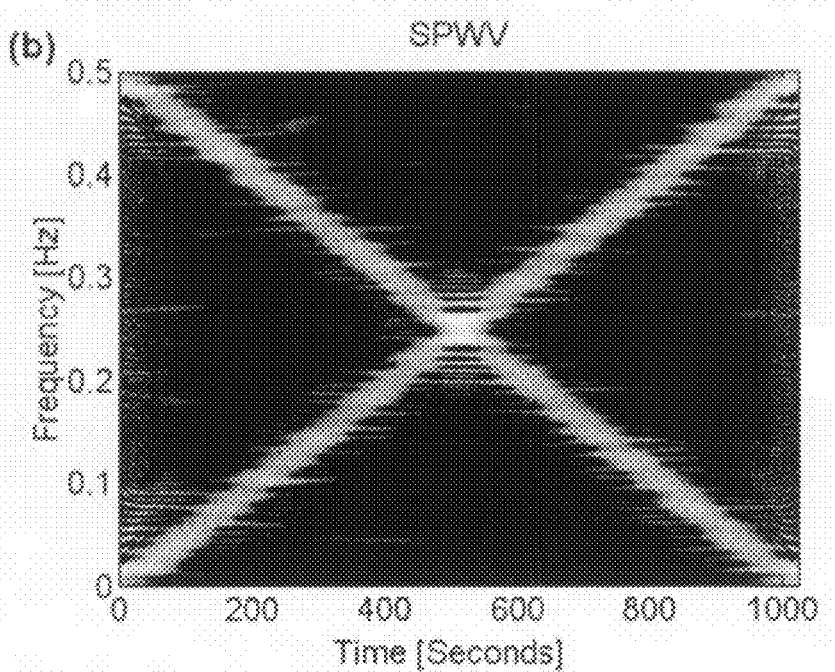
Figure 3C:
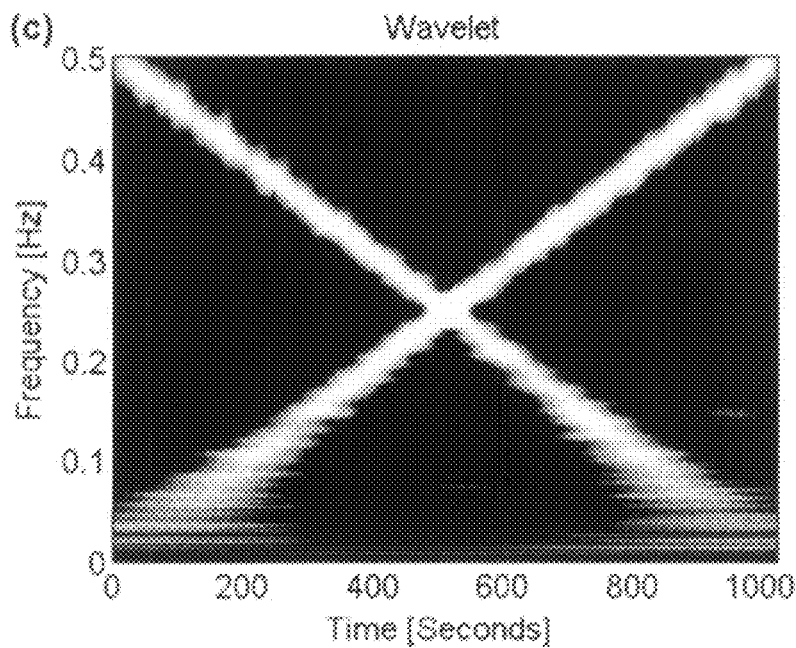

FIG. 3B shows the spectrum dispersion of the SPWV due to many cross term artifacts. With the CWT (FIG. 3C), time-frequency resolution is variable as the time resolution degrades with decreasing frequencies.

Figure 3D:
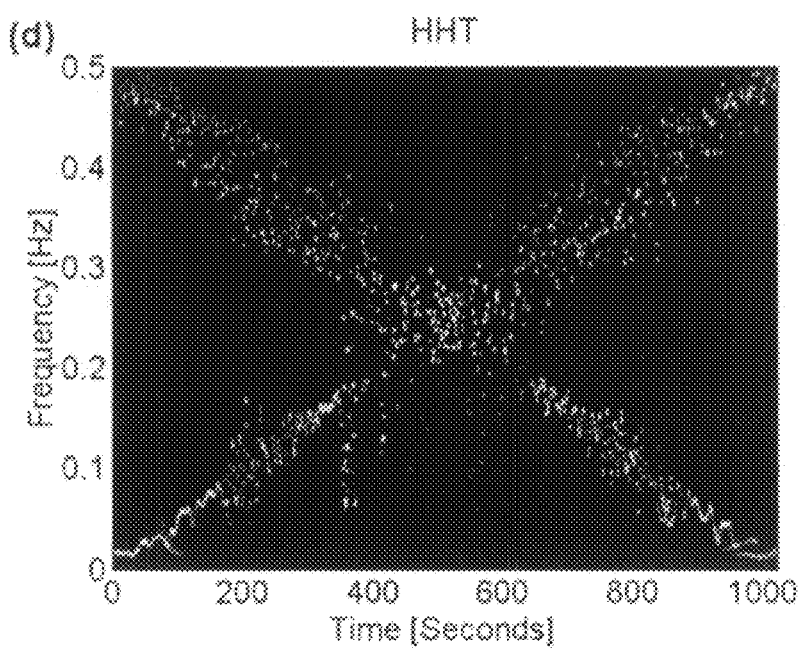
Figure 3E:
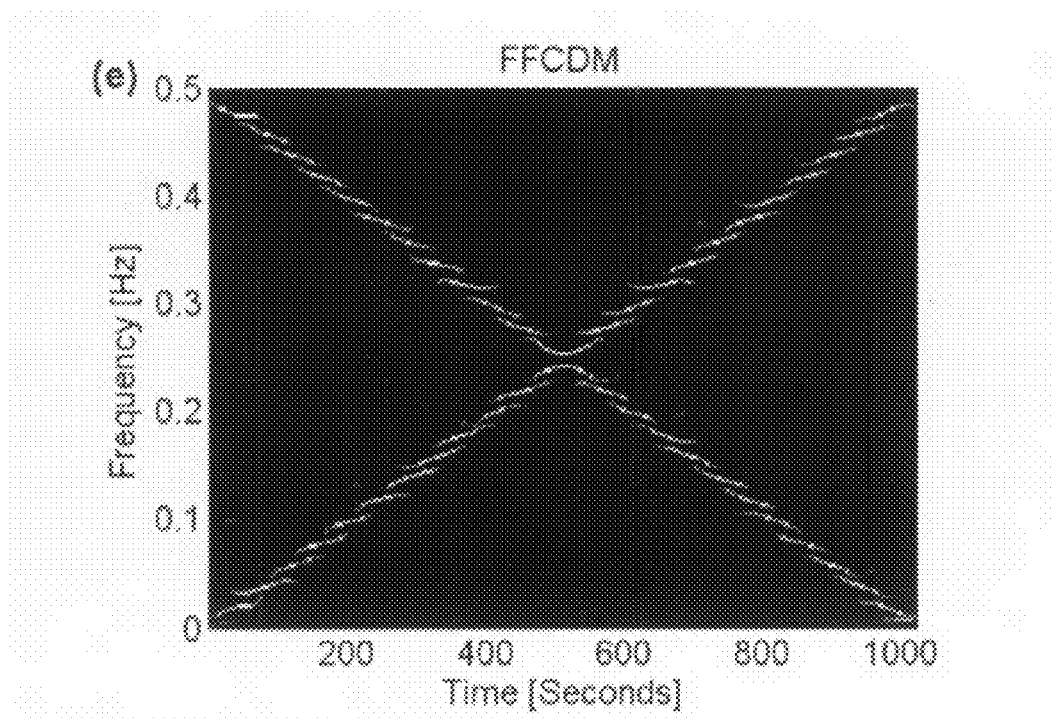
Figure 3F:
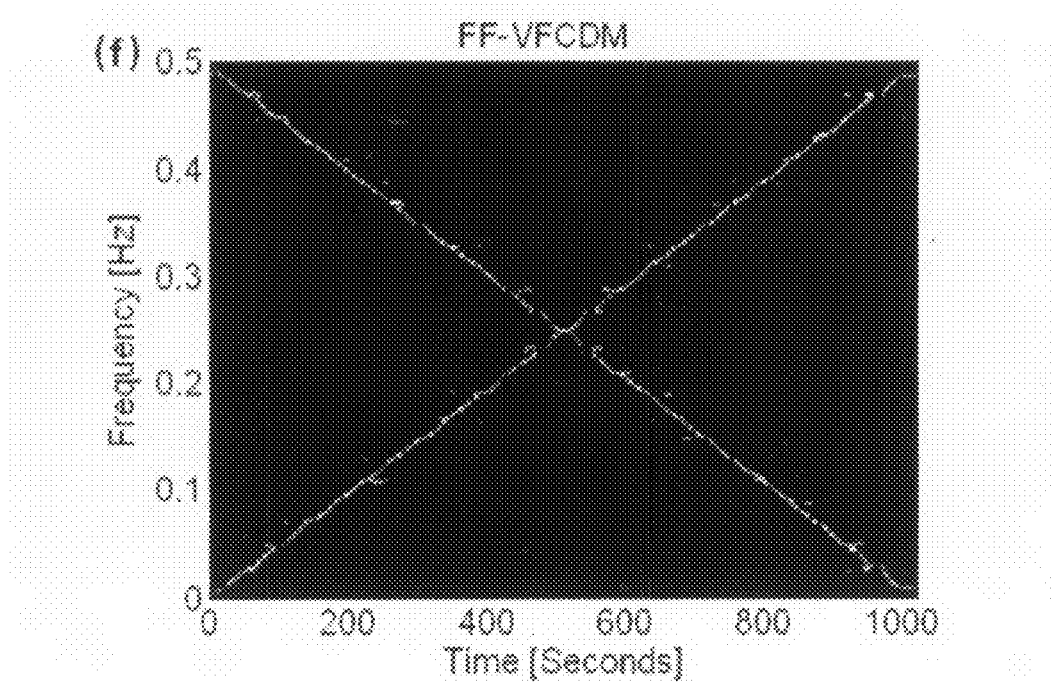
Figure 3G:
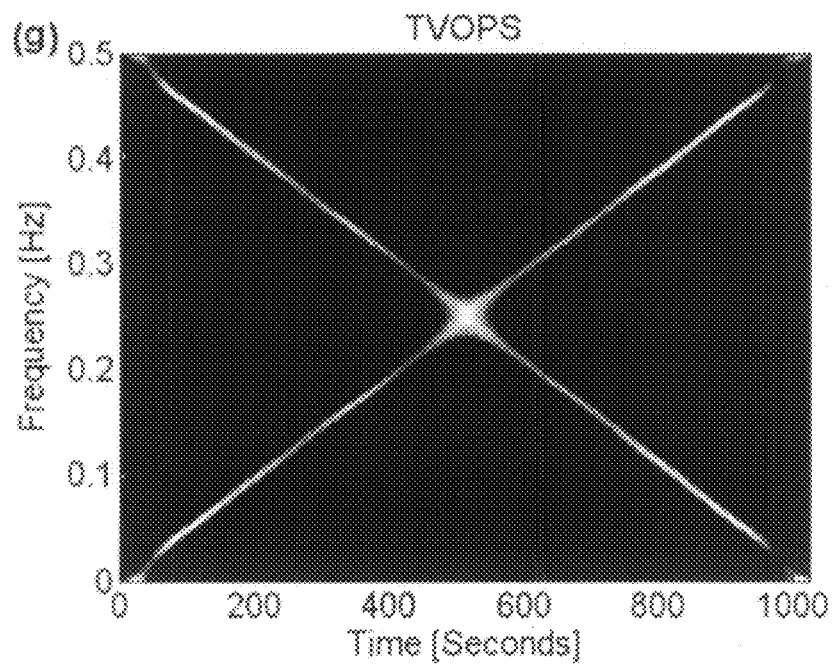
Figure 3H:
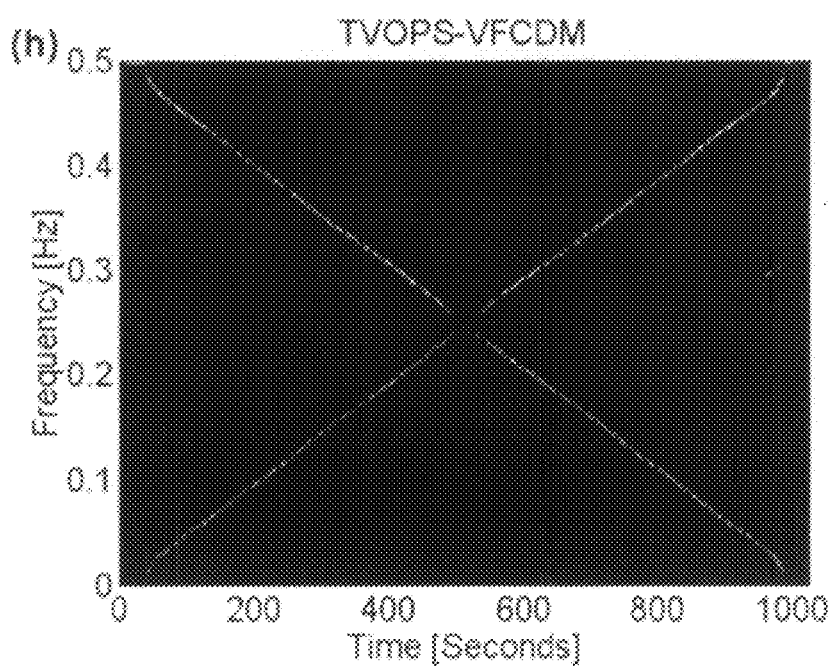

In FIG. 3D, HHT fails to show a clear cross-shaped spectrum because the HHT method is especially sensitive to noise, as previously demonstrated. FIG. 3E, obtained by the FFCDM (with $N_\omega=128$, $F_\omega=0.01$ Hz ($f_{0_j}=0+(i-1)(0.02)$ Hz)), shows dispersions along the cross-shaped lines due to the problems associated with the edge effect of the LPF. FIG. 3F, obtained via the FF-VFCDM, shows fine TF resolution, and with less dispersion along the crossed lines than FIG. 3E. The length of the LPF, its bandwidth, and the bandwidth of the variable frequency were set to: $N_\omega=128$, $F_\omega=0.02$ Hz ($f_{0_j}=0+(i-1)(0.04)$ Hz) and $F_v=0.01$ Hz, respectively. The TVOPS-based spectrum also provides high TF resolution, shown in FIG. 3G, albeit at slightly less TF resolution than the FF-VFCDM, and without any dispersion along the backbones of the cross-shaped spectrum. The TVOPS-VFCDM based spectrum shown in FIG. 3H provides the best time and frequency resolution than any of the methods compared.

Figure 4A:
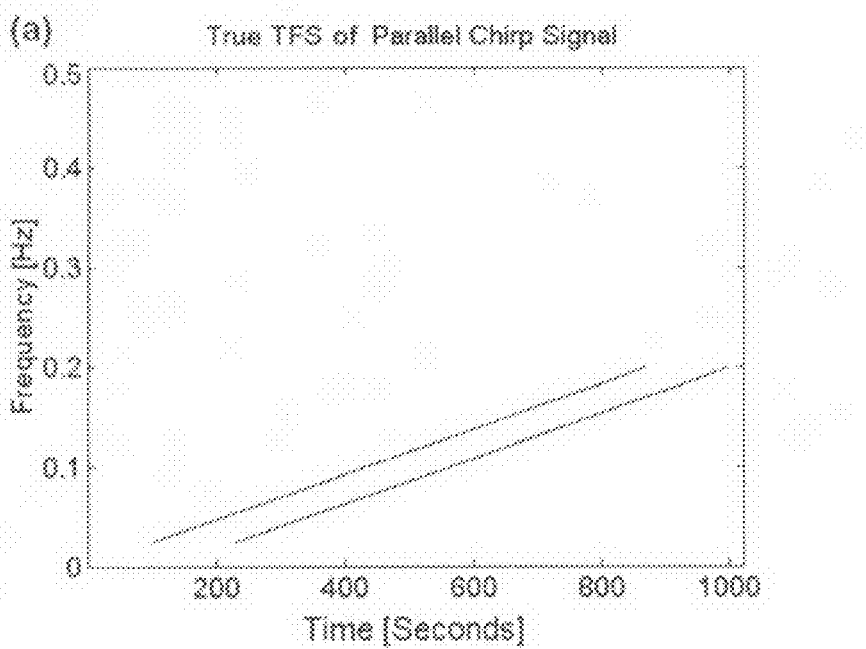
FIGS. 4A-H provide a time-frequency analysis of a parallel chirp signal contaminated by 10 dB additive Gaussian white noise.
Figure 4B:
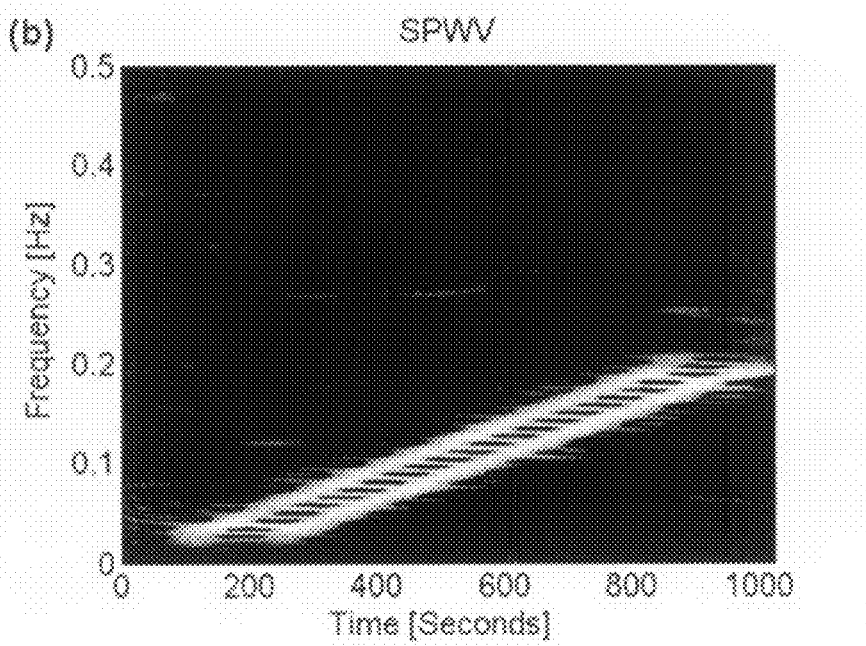
Figure 4C:
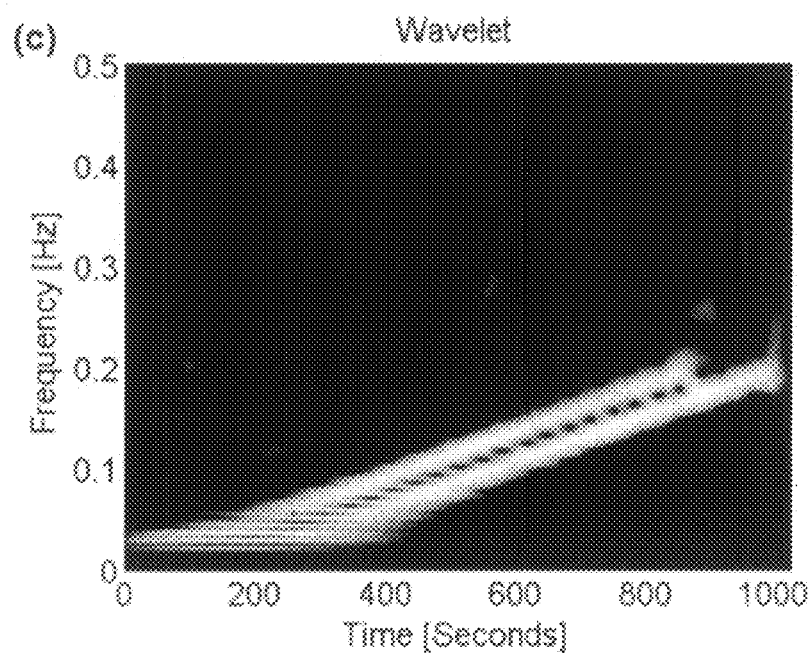
Figure 4D:
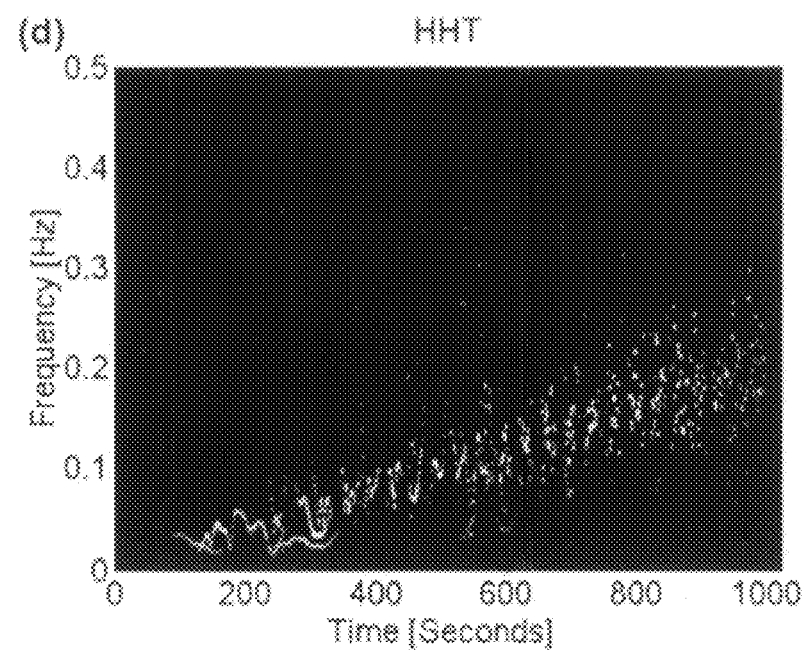
Figure 4E:
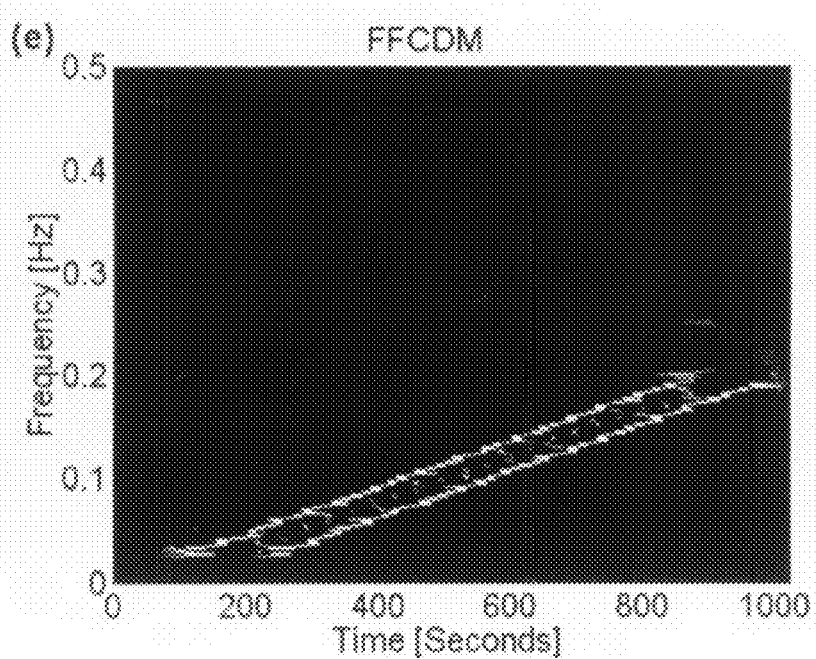
Figure 4F:
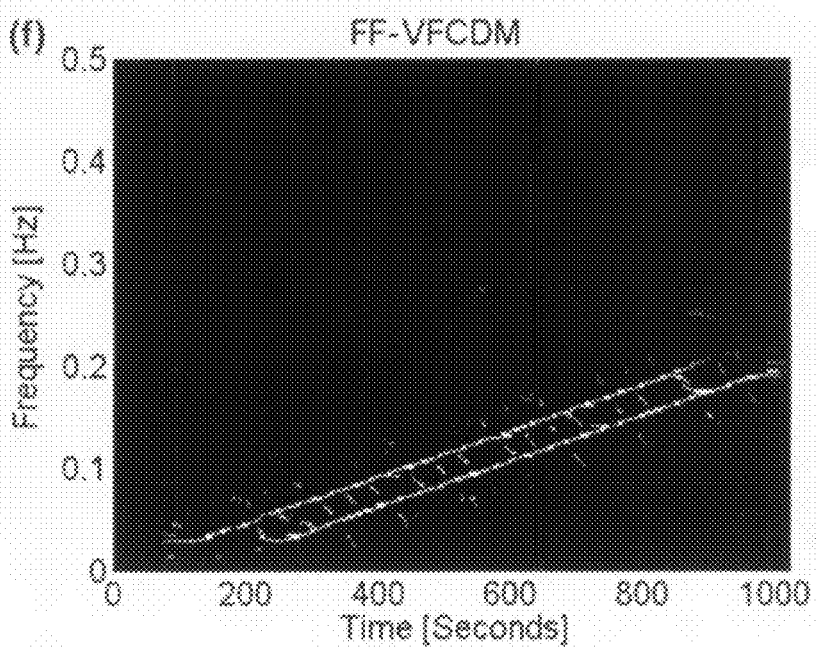
Figure 4G:
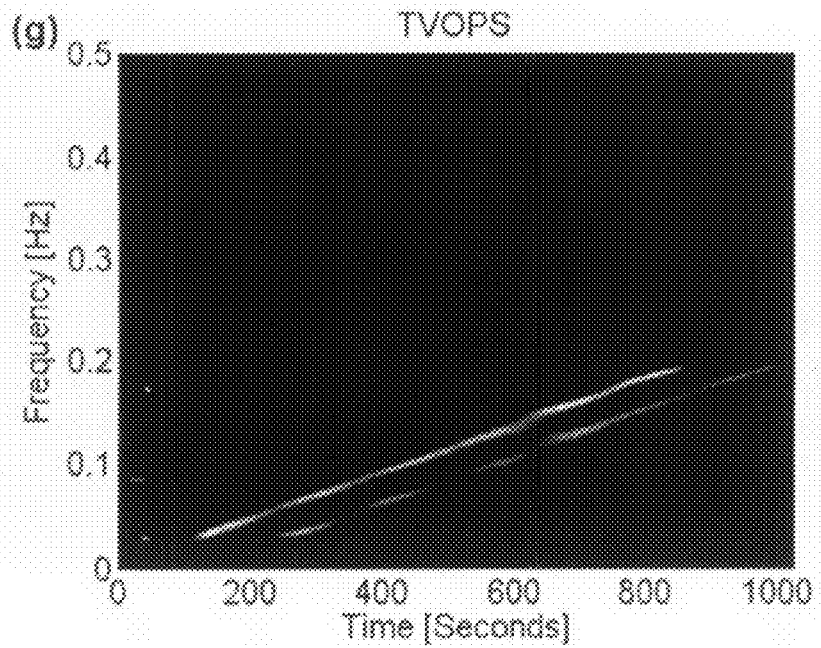
Figure 4H:
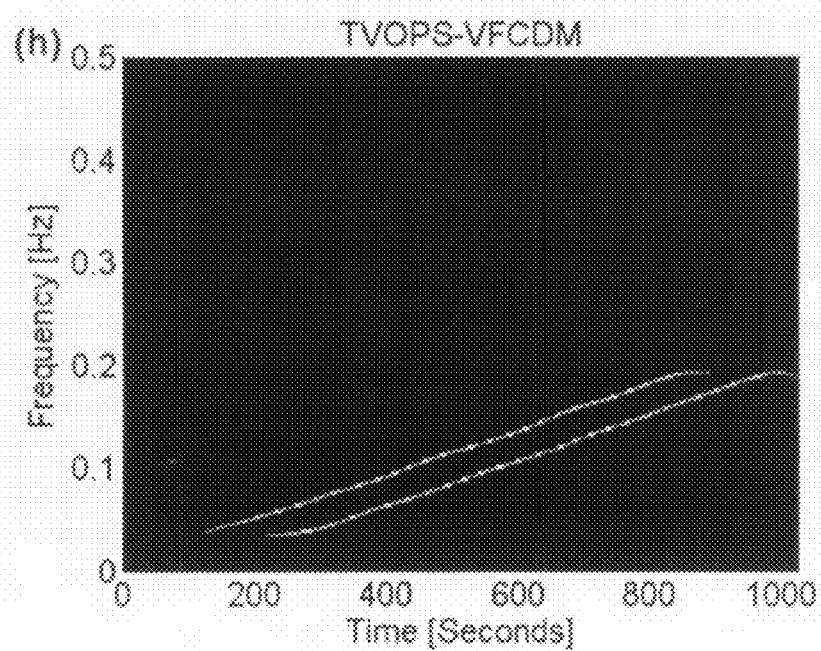

In the second example, a closely spaced parallel chirp signal was utilized, corrupted with 10 dB additive Gaussian white noise, to illustrate the advantages of using the TVOPS-VFCDM over the FF-VFCDM. In addition, comparison to the SPWV, CWT, HHT, FFCDM and TVOPS methods are made. The pure TF spectrum (without additive Gaussian white noise contamination) is shown in FIG. 4A. The signal contains two chirp signals with frequencies increasing from 0.025 Hz to 0.2 Hz. The first chirp signal starts at 100 seconds and ends at 871 seconds, while the other one begins at 230 seconds and ends at 1001 seconds. Estimated TF spectra of the SPWV, CWT, HHT, FFCDM, FF-VFCDM, TVOPS, TVOPS-VFCDM are shown in FIGS. 4B-H, respectively. The filtering settings are: $N_\omega=128$, $F_\omega=0.005$ Hz $\{f_{0_j}=0+(i-1)(0.01)$ Hz$\}$ for the FFCDM and $N_\omega=128$, $F_\omega=0.01$ Hz, $F_v=0.005$ Hz for the FF-VFCDM and TVOPS-VFCDM. As in the first example, the SPWV, CWT and HHT performances are not on par with the TVOPS, FF-VFCDM and TVOPS-VFCDM. Significant dispersion can be seen along the parallel lines with SPWV and CWT, whereas for HHT, these parallel lines are not discernible. There is considerable improvement in delineating the parallel lines with the FFCDM, FF-VFCDM, TVOPS and TVOPS-VFCDM methods, and the least dispersion was found with TVOPS-VFCDM.

Figure 5:
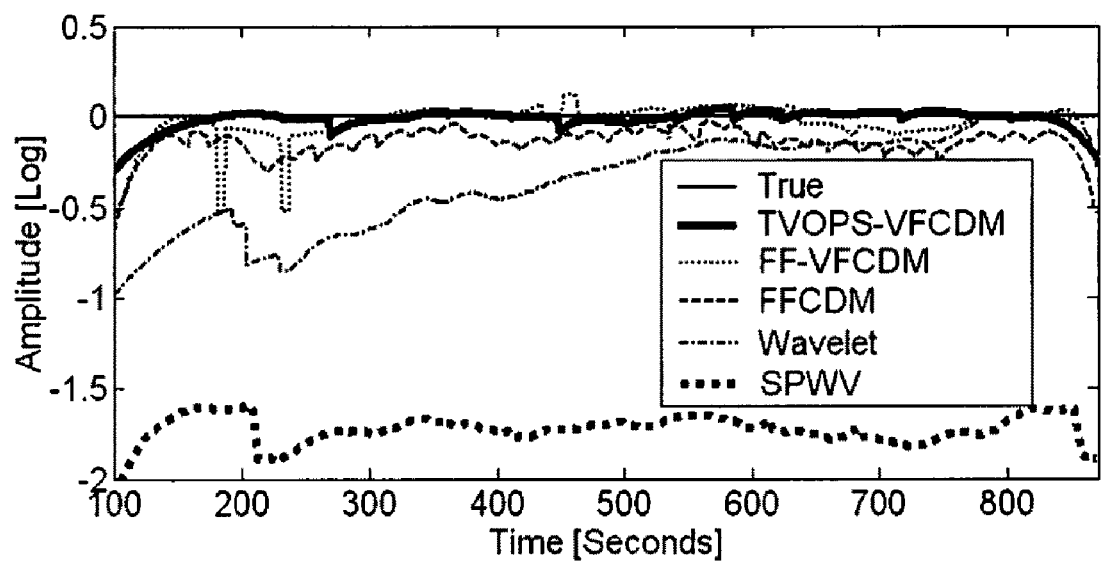
FIG. 5 compares estimated spectral amplitudes of different methods.

In regard to the parallel chirp signal shown in FIG. 4A, an examination of the ability of the time-varying spectral methods to estimate the true magnitude of the signal is made. FIG. 5 compares five different methods: SPWV (thick dotted line), CWT (thin dash-dotted line), FFCDM (thin dashed line), FF-VFCDM (thin dotted line) and the TVOPS-VFCDM (thick solid line). The true amplitude (thin solid line) of the signals (two chirp signals) are 0 in a logarithmic scale, as we are mainly concerned with estimating the instantaneous amplitude as a function of time for the top chirp signal that starts at 100 seconds and ends at 871 seconds, with frequencies increasing from 0.025 Hz to 0.2 Hz. The SPWV provides the least accurate estimation of the true amplitude of the signal. For the CWT, the estimation of the amplitude especially at low frequencies is suspect, since CWT suffers from poor time resolution at low frequencies. The FF-VFCDM provides accurate estimation of the true amplitude, although at certain time points (e.g., ~180 and ~220 seconds), the amplitude values show noticeable deviation from the true amplitude. Note also the greater accuracy in the estimated amplitude with the FF-VFCDM method than the FFCDM. As described earlier (see FIG. 2), due to edge effects of the low-pass filter, the FFCDM does not provide as accurate estimation of the instantaneous amplitudes as does the FF-VFCDM.

As in the first simulation example, the TVOPS-VFCDM approach provides the best amplitude estimation of any of the methods compared since the amplitude values are very close to the exact value of 0 dB for all times. In this plot, results from the TVOPS and HHT are missing since it is well known that model-based approaches such as the TVOPS do not preserve the true amplitude of signal, and HHT is not shown because it is highly affected by the noise contamination for this particular example.

Renal auto regulatory mechanisms are identified as follows. The above-described experimental methods were conducted on male Sprague-Dawley Rats (SDR) and male Spontaneously Hypertensive Rats (SHR) (200-300 g) in accordance with institutional guidelines for the care and use of research animals. The rats had free access to food and tap water before the experiments. After induction of anesthesia by Inactin (Sigma), a rat was placed on a temperature-controlled surgery table, which maintained body temperature at 37° C. The left femoral artery and vein were catheterized (PE-50 and PE-10 tubing) for measurement of arterial pressure and continuous infusion of saline, respectively. The left kidney was isolated and placed in a Lucite cup and the cortical surface was covered with a thin plastic film to prevent evaporation. The renal perfusion pressure was controlled with a supra-renal aortic clamp. Cortical blood flow (CBF) was measured with a laser-Doppler instrument (Transonic, Ithaca, N.Y.) with a blunt 11-gauge needle probe placed on the cortical surface. Following a 3-5 minute recording of CBF at spontaneous blood pressure (BP), the aortic clamp was adjusted to reduce Renal Arterial Pressure (RAP) by 20 to 30 mmHg below spontaneous BP. After CBF stabilized (typically 1 minute), the clamp was quickly released and the resulting transient CBF data were recorded. The resulting CBF as measured with the laser Doppler probe is shown in the panels below the BP measurements, expressed in tissue perfusion units (TPU). Data analysis is based on 7 SDR and 7 SHR recordings. Each of the experimental data records used for analysis was 350 seconds in length, with a sampling rate of one sample per second, after digital low-pass filtering to avoid aliasing.

The procedure for the estimation of instantaneous amplitudes for the combined TVOPS-VFCDM methods is as follows: 1) extract the instantaneous frequencies associated with the TubuloGlomerular Feedback (TGF) and myogenic mechanisms using TVOPS in the frequency bands associated with these two renal auto regulatory mechanisms: 0.02 to 0.05 Hz (TGF), and 0.1 to 0.2 Hz (myogenic); 2) use the VFCDM method to obtain a complex demodulated signal with the following parameter settings for the low-pass filter: $N_\omega=128$, $F_v=0.005$ Hz ($f_{o_i}=0+(i-1)(0.01)$ Hz) so that an instantaneous amplitude estimation can be obtained. Frequency bands at 0.02 to 0.05 Hz and 0.1 to 0.2 Hz are considered to be characteristic frequencies of the TGF and myogenic mechanisms, respectively, as these frequency bands have been previously characterized. The amplitudes of TGF and the myogenic mechanism physiologically represent the volumetric flow rate in the surface of a kidney as measured by a laser-Doppler flow probe.

Figure 6:
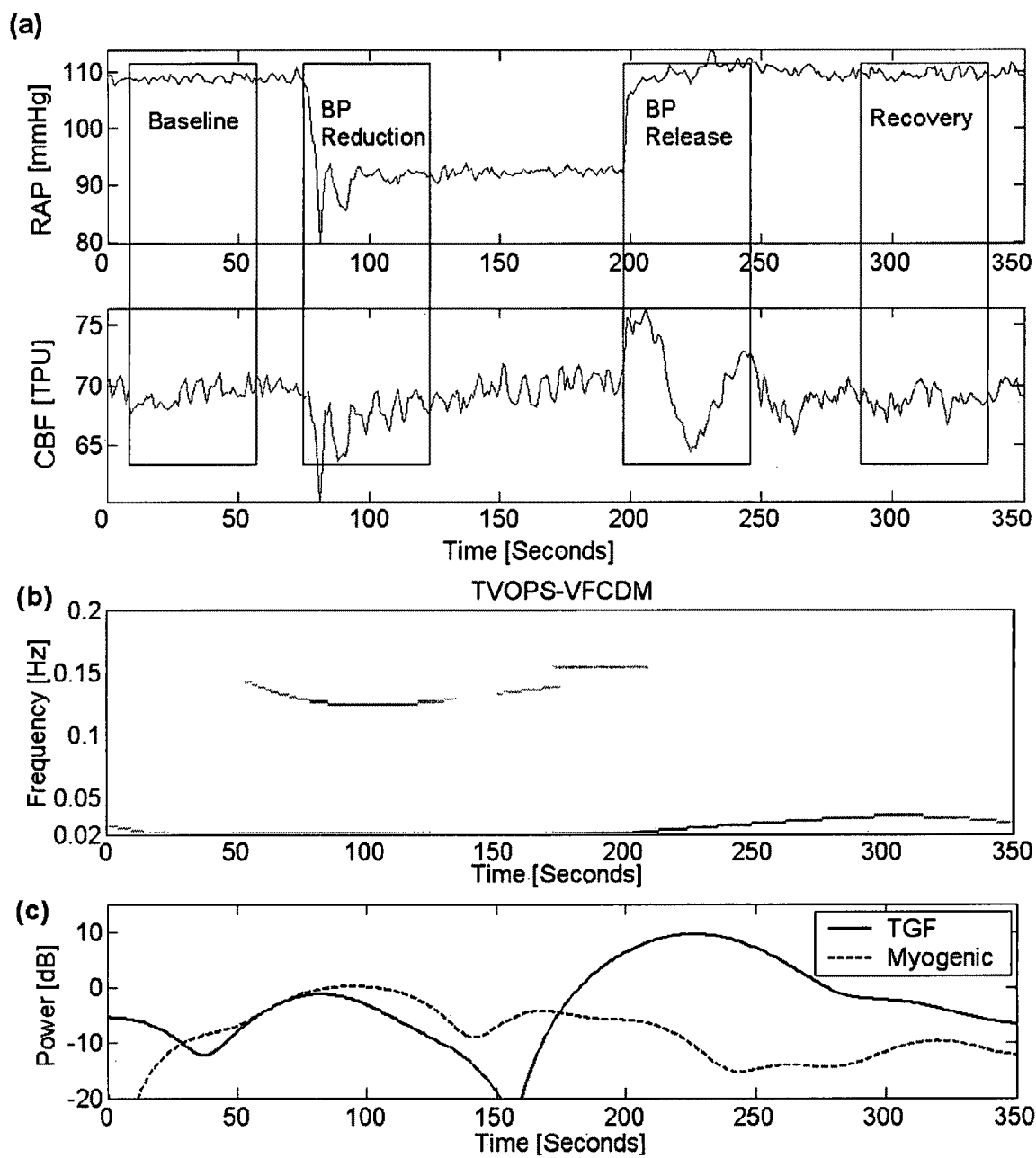
FIGS. 6A-C provide time-frequency analysis of one Sprague-Dawley Rat (SDR) data sets.
Figure 7:
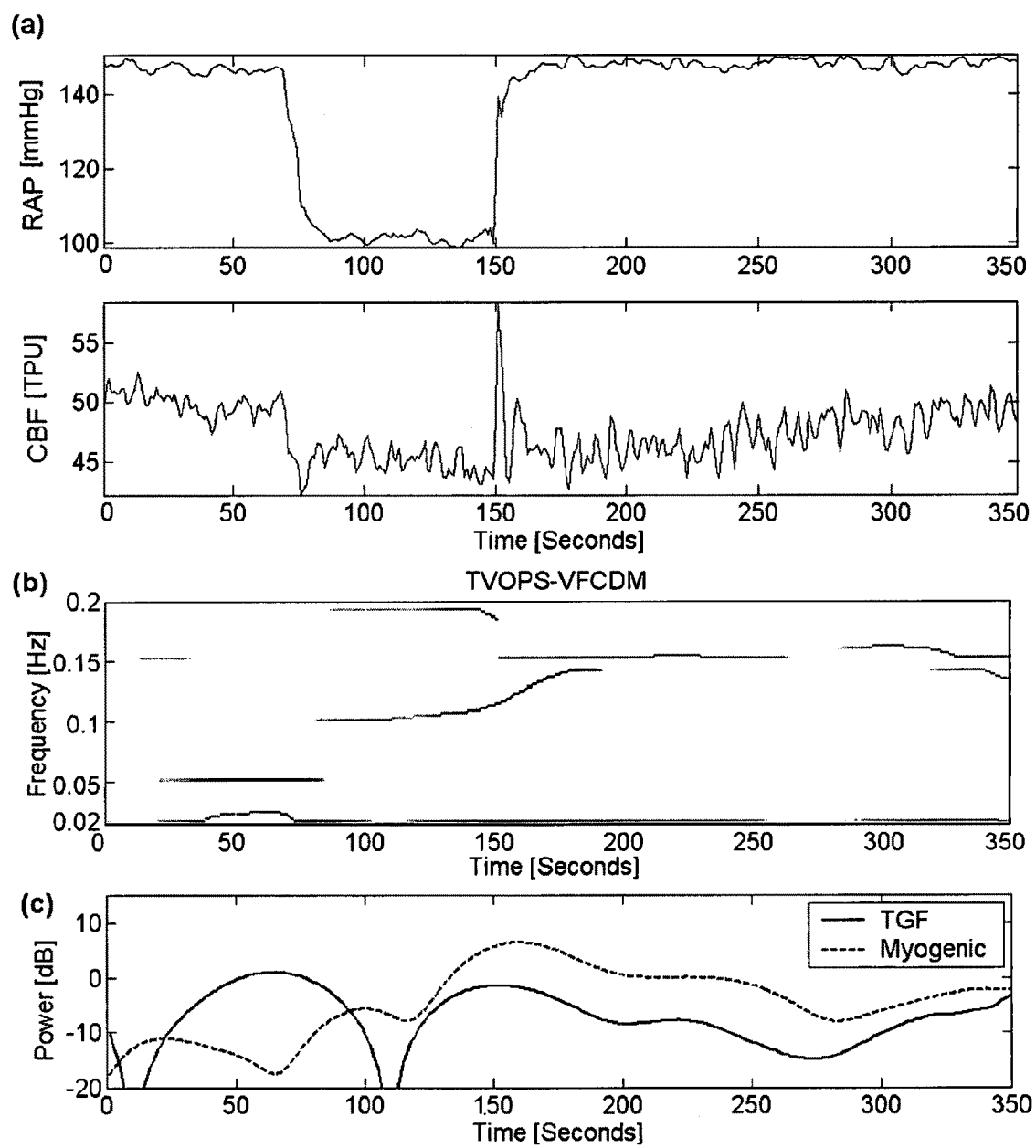
FIGS. 7A-C provide a time-frequency analysis of a Spontaneously Hypertensive Rat (SHR) data set.

Representative results based on 7 SDR and 7 SHR recordings are shown in FIGS. 6 and 7, respectively. The top and bottom panels of FIGS. 6A (SDR) and 7A (SHR) represent the measurements of RAP and CBF, respectively. Results based on the use of TVOPS-VFCDM on the CBF data are shown in FIG. 6B for SDR and FIG. 7B for SHR. Both FIGS. 6B and 7B clearly show oscillations around 20~50 mHz and 100~200 mHz, which suggest strong TGF and myogenic activations, respectively. FIGS. 6C and 7C show fluctuations of power (obtained by squaring amplitudes) for frequencies associated with the myogenic and TGF mechanisms using TVOPS-VFCDM for SDR and SHR, respectively.

Time segments of the CBF signal, indicated by the rectangular boxes in FIG. 6A, were used to compare the magnitude of TV power spectral density during the four stages: baseline, BP reduction, BP release and recovery. In both FIGS. 6A and 7A, the overshoot in flow rate after BP release is a reflection of the afferent arterioles distending to allow blood flow to increase with a sudden increase in BP. The overshoot in flow rate is then compensated for, first by the myogenic mechanism, and then by TGF, to achieve a steady-state flow rate. To discern quantitative differences in the amplitudes in these four stages, the average amplitudes (based on 7 recordings each from SDR and SHR) of TGF and the myogenic mechanism were calculated, and are shown in FIG. 8A for SDR and FIG. 8B for SHR. The randomized block ANOVA was performed ($\alpha=0.05$) to test whether there are significant differences among the myogenic and TGF mechanisms from the SDR and SHR in the four stages. There are significant differences for the TGF mechanism ($p<0.001$) in the four stages for both SDR and SHR. Similar statistical differences ($p<0.001$) were also found for the myogenic mechanism in the four stages for both strains of rats.

The Student-Newman-Keuls test was performed ($\alpha=0.05$) to examine the differences between all possible pairs of the four stages. For the TGF amplitudes of the SDR, BP release>BP reduction>Baseline=Recovery, and for the SHR, BP release=BP reduction>Baseline=Recovery. For the myogenic amplitudes of the SDR, BP reduction=BP release>Recovery=Baseline, and for SHR, BP release>BP reduction>Baseline=Recovery. This is shown graphically in Table 1 below, which provides a statistical comparison of the myogenic and TGF mechanisms in the four experimental stages for SDR and SHR.

TABLE 1

| TGF | SDR | BP release > BP reduction > Baseline = Recovery |
| Myogenic | SDR | BP reduction = BP release > Recovery = Baseline |
| TGF | SHR | BP release = BP reduction > Baseline = Recovery |
| Myogenic | SHR | BP release > BP reduction > Baseline = Recovery |

TABLE 1 indicates that in both SDR and SHR, there is no significant difference between Baseline and Recovery stages for both the TGF and myogenic mechanisms. When the BP is either reduced or increased (released), TGF and myogenic activities are significantly stronger than the baseline for both SDR and SHR. In SDR, TGF activity is significantly stronger in BP release than in BP reduction ($p<0.001$), and in SHR, myogenic is significantly stronger in BP release than in BP reduction (p<0.001). In summary, these results suggest that TGF is more sensitive to increased BP than to reduced BP in SDR rats. Furthermore, during BP release, TGF power is greater than myogenic in SDR (paired t-test, p<0.001), but the opposite is the case for SHR (paired t-test, p<0.05). A consequence of this greater TGF power in SDR during BP release is that this power decreases exponentially (r=0.91, p<0.001), but no such exponential decrease in TGF power is observed in SHR.

Figure 8:
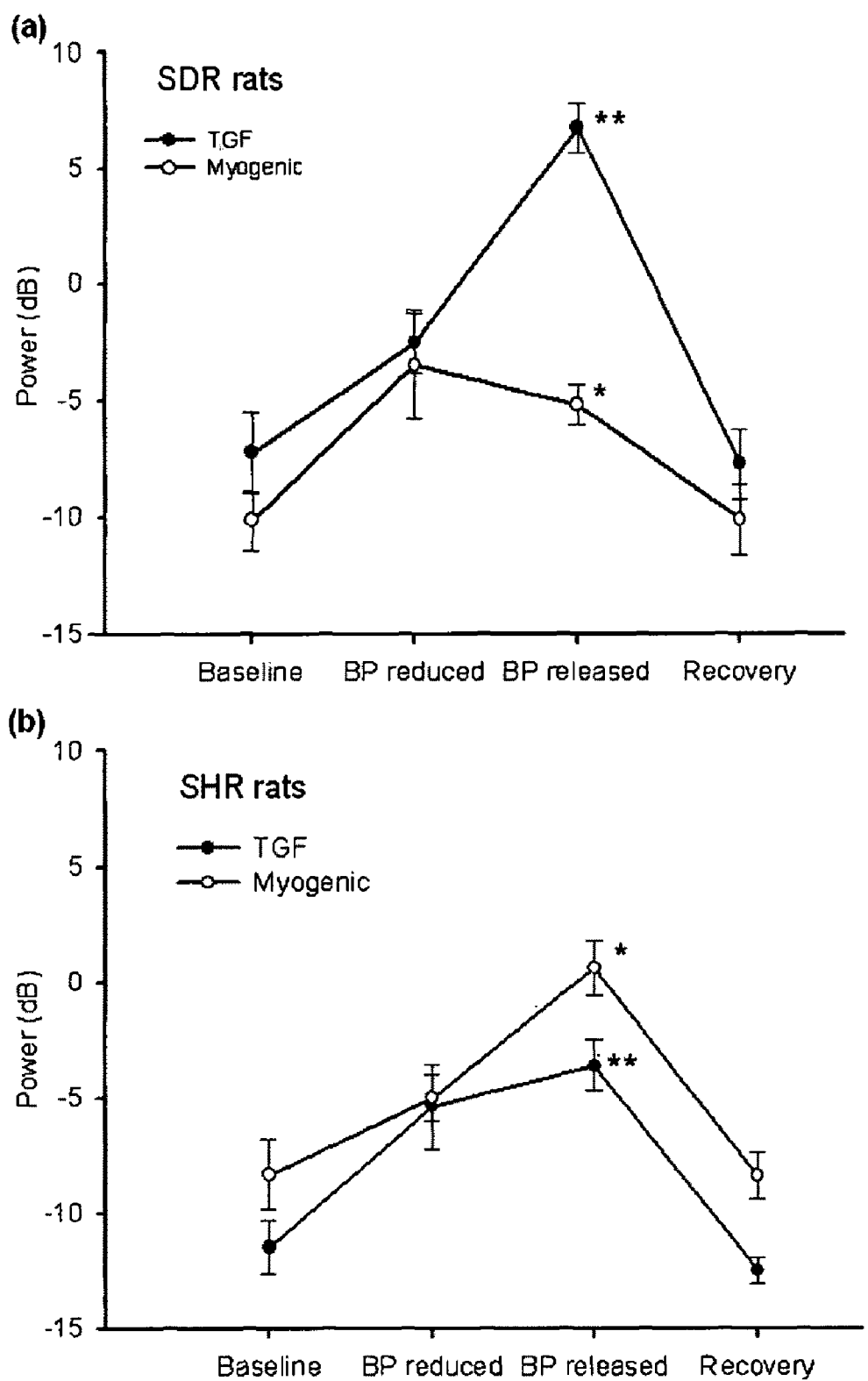
FIGS. 8A-B are power spectral amplitude charts of TubuloGlomerular Feedback (TGF) and myogenic mechanisms in the different stages.

Comparing between SDR and SHR, it was found that the myogenic amplitudes were significantly greater in SHR during BP release conditions. FIG. 8 is a chart of power spectral amplitude of TGF and myogenic mechanisms, showing mean±standard error in the different stages of SDR (normotensive) rats in FIG. 8A and SHR (hypertensive) rats in FIG. 8B, where * represents significant difference between the myogenic power of SDR and SHR during BP release, t-test, p=0.002, and  represents significant difference between the power of TGF of SDR and SHR during BP release, t-test, p<0.001. For TGF, it was found that SDR have statistically greater amplitudes than SHR (FIG. 8, , t-test, p<0.001) during BP release conditions. Other conditions resulted in no statistical differences between SDR and SHR.

Extraction of respiratory rate via the method of the present invention provides advantages when combined with medical devices such as a pulse oximeter (see, U.S. Pat. No. 7,206,621, the contents of which are incorporated herein by reference), to provide improved diagnosis and treatment of sleep apnea, replacement electrocardiograph signal, sudden infant death syndrome; and hypovolemia and hypovolemic conditions. In such embodiment, only one sensor is needed to extract many important vital signals instead of using many different sensors. For example, to extract respiratory rate utilizing a conventional apparatus, a separate breathing sensor is needed to obtain accurate measurements. This limitation is overcome by using a recently developed a general-purpose signal-processing algorithm (See, R. Zou, et al., cited above). The key to extracting accurate respiratory rate from pulse oximeter data is recognizing that breathing rate modulates heart rate in the form of Frequency Modulation (FM). Normally, identification of this FM is difficult due to non-stationary nature of the data, noise, and motion artifacts. The general-purpose signal-processing algorithm, overcomes the aforementioned problems. The general-purpose signal-processing algorithm is a time-varying method, and provides one of the highest spectral resolution, which enables the detection of the FM peak in the time-varying spectrum. An FM peak near the heart rate peak is detected using the general-purpose signal-processing algorithm.

The general-purpose signal-processing algorithm is implemented in real-time to provide accurate Respiratory Rate (RR) values every 5 seconds. Commercial monitors using ECG-derived respiratory rate update RR values every 5 seconds. The technology is more cost effective since additional sensors are eliminated, other than the pulse oximeter. In addition, using only a pulse oximeter sensor greatly enhances patient comfort during data collection since both ECG and respiratory sensors restrict any unnecessary movements. For example, during sleep apnea detection, a patient's comfort is greatly increased since no mask or ECG leads are required. The method described herein is applicable to any conditions/diseases related to respiratory disease whereby monitoring respiratory rate is important. For example, a pulse oximeter, which is a standard monitor device that is ubiquitous in many hospitals and nursing homes, can be retrofitted for use according to the current invention.

Figure 9:
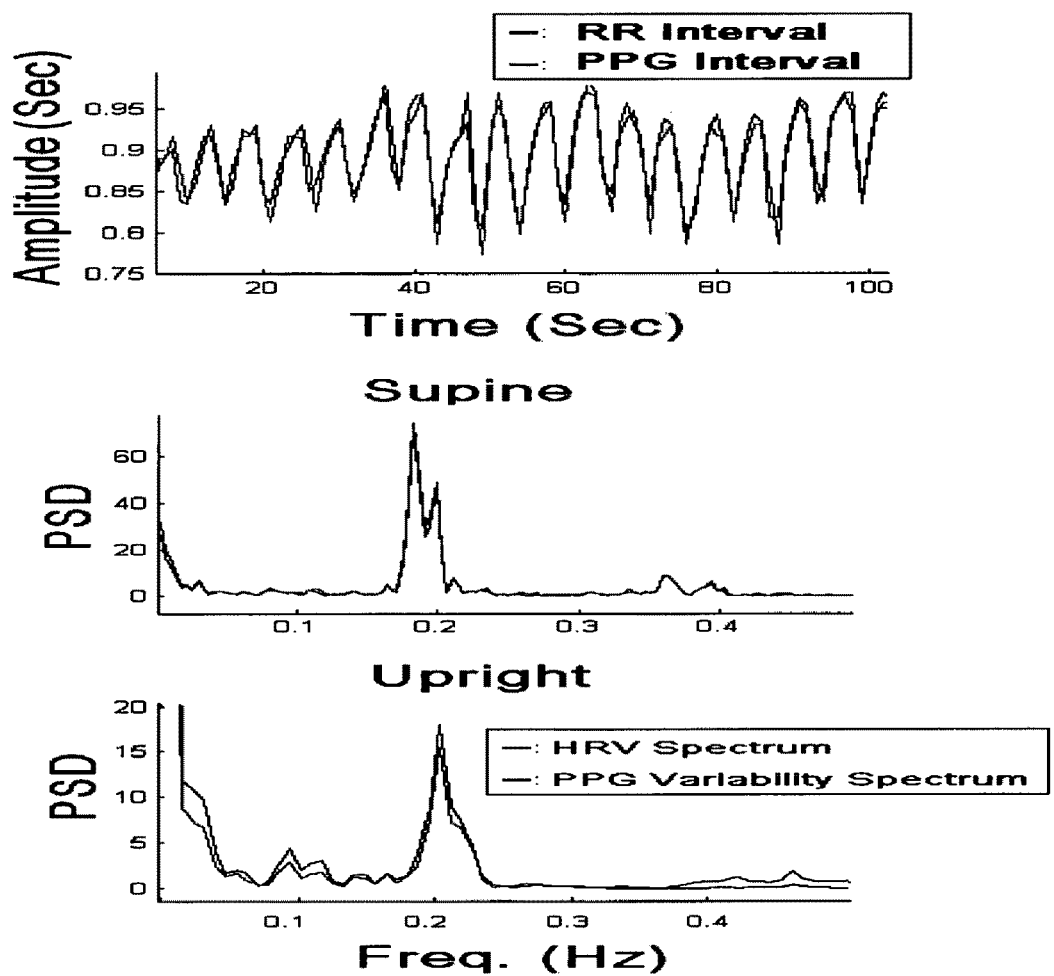
FIG. 9 provides a comparison of Respiratory Rate (RR) and PPG interval data (top panel), and provides power spectral density plots of the RR and PPG interval data for supine (middle panel) and upright (bottom panel) positions.
Figure 10:
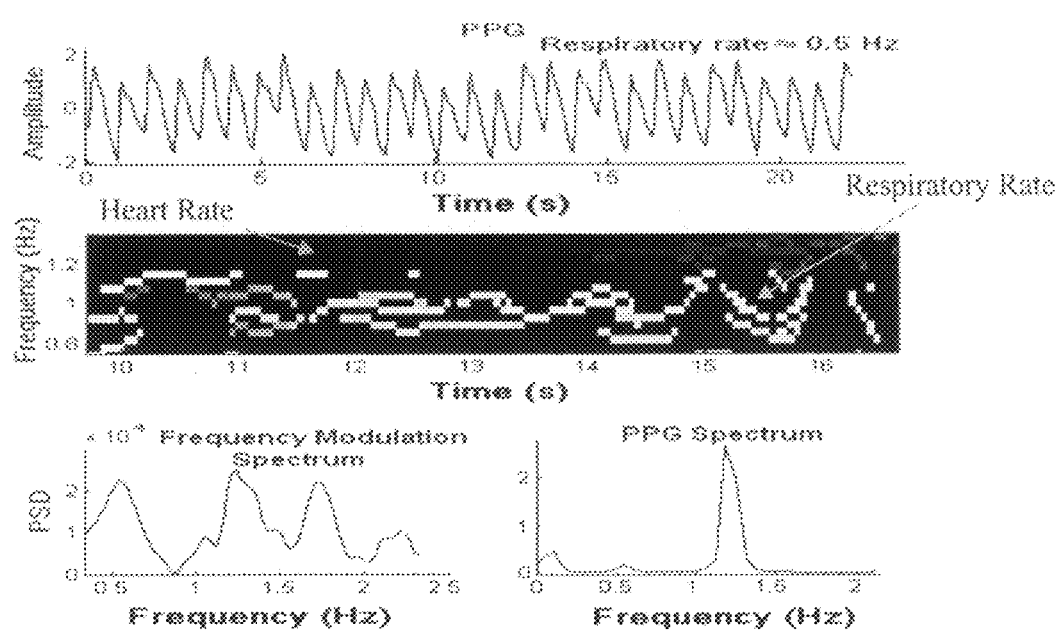
FIG. 10 provides a comparison of respiratory rate extraction from a PPG signal (top panel) via the VFCDM (middle and bottom left panels) and power spectral densities (bottom right panel) methods.

Respiratory Rate (RR) is obtained from an ECG recording via estimation of the power spectral density of the RR interval data, and its spectral peak is often reflected in the high frequency band (0.15-0.4 Hz). To examine if RR and the dynamics of the autonomic nervous system are also reflected in the spectrum of the PPG variability data, simultaneous measurements of ECG and PPG signals were obtained from a subject in both supine and upright positions for a five-minute duration. Both RR and PPG interval data were extracted from raw ECG and PPG signals, respectively, for both positions. During measurements, the number of spontaneous breaths was counted for every minute to verify the accuracy of respiratory rate extracted from the power spectrum. The top panel of FIG. 9 shows comparison of the ECG derived RR and pulse oximeter derived PPG intervals. These two signals are nearly identical to each other as they mirror the rise and fall values of each other's respective signals. A representative spectra (2 minutes of PPG and RR interval data) for both postures are shown in the middle and bottom panels of FIG. 9. Also shown in FIG. 9 are the simultaneously measured ECG and the processed spectra of the heart rate data. Respiratory rate was 12 breaths/min (0.2 Hz) for this data, and the corresponding spectra show a well-defined peak at 0.2 Hz for both postures. The spectral dynamics of the PPG interval data are nearly identical to the heart rate interval data across all frequencies for both postures. These preliminary examinations suggest that PPG interval data can be used instead of R-R interval data to determine the dynamics pertaining to the autonomic nervous system. Further, accurate respiratory rate can be obtained using the PPG interval data via the analysis of power spectrum.

The effect of oxygen saturation on the PPG signal was also examined by having a subject breath 100% oxygen enriched gas delivered with a bias flow of 4-6 l/min for a duration of 5 minutes. This led to an increase of oxygen saturation reading from 97-98% to 100% on a commercial pulse oximeter (Nelcor). The data analyses described in the previous paragraph were carried out. The accuracy of respiratory rate calculations and dynamics of the autonomic nervous system were found not to be compromised by oxygen saturation.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A digital filtering method for estimating Time-Frequency Spectra (TFS) and associated amplitudes of a photoplethysmography (PPG) signal using Variable Frequency Complex Demodulation (VFCDM), the method comprising:
obtaining a first TFS of the PPG signal by performing, with a controller, a time-varying optimal parameter search;
performing, with the controller, the VFCDM with the first TFS of the PPG signal to obtain at least one variable frequency complex demodulation signal having improved TFS resolution and instantaneous amplitudes associated with only specific frequencies of interest; and
simultaneously deriving, with the controller, a heart rate and a respiratory rate of a subject from the at least one variable frequency complex demodulation signal.

2. A photoplethysmography (PPG) apparatus for monitoring heart and respiratory rates, the apparatus comprising:
a controller configured to:
obtain a first Time-Frequency Spectra (TFS) of a PPG signal by performing a time-varying optimal parameter search, perform a Variable Frequency Complex Demodulation (VFCDM) with the first TFS of the PPG signal to obtain at least one VFCDM signal having improved TFS resolution and instantaneous amplitudes associated with only specific frequencies of interest, and simultaneously derive a heart rate and a respiratory rate of a subject from the at least one VFCDM signal.

3. The apparatus of claim 2, wherein the apparatus is configured to provide improved diagnosis treatment of sleep apnea.

4. The apparatus of claim 2, wherein the apparatus is configured to provide an electrocardiograph signal.

5. The apparatus of claim 2, wherein the apparatus is configured to detect sudden infant death syndrome.

6. The apparatus of claim 2, wherein the apparatus is configured to detect hypovolemia.

7. The apparatus of claim 2, wherein the apparatus is configured to determines renal blood flow data.

* * * * *